(12) United States Patent
Grund et al.

(10) Patent No.: US 6,613,946 B2
(45) Date of Patent: *Sep. 2, 2003

(54) PROCESS FOR PREPARING CYCLIC ALCOHOLS

(75) Inventors: Gerda Grund, Duelmen (DE); Bernd Guenzel, Haltern (DE)

(73) Assignee: Degussa AG, Duesseldorf (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/425,011

(22) Filed: Oct. 25, 1999

(65) Prior Publication Data

US 2002/0004616 A1 Jan. 10, 2002

(30) Foreign Application Priority Data

Oct. 22, 1998 (DE) .......................... 198 48 730

(51) Int. Cl.[7] ............................. C07C 45/27; C07C 35/02
(52) U.S. Cl. ....................................... 568/359; 568/821
(58) Field of Search ................................ 568/338, 359, 568/821; 561/357

(56) References Cited

U.S. PATENT DOCUMENTS

| 3,488,740 A | | 1/1970 | Russell | |
|---|---|---|---|---|
| 4,263,453 A | | 4/1981 | Schulz et al. | |
| 4,322,558 A | * | 3/1982 | Risebury | 568/359 |
| 4,341,907 A | * | 7/1982 | Zelonka | 568/376 |
| 4,933,508 A | * | 6/1990 | Habu et al. | 568/832 |
| 5,767,320 A | | 6/1998 | Raja et al. | |

FOREIGN PATENT DOCUMENTS

| BE | 668.681 | 12/1965 |
|---|---|---|
| DE | 552 886 | 4/1934 |
| EP | 0 519 569 | 12/1992 |
| FR | 1.486.391 | 5/1967 |
| FR | 1.549.178 | 12/1968 |
| GB | 1035624 | 7/1966 |

OTHER PUBLICATIONS

CA:75:98236 abs of DE2101633 Jul. 1971.*
CA:89:42025 abs of Zh. Prikl Khim (Leningrad) by Moskovich et al 51(5) pp. 1137–1140 1978.*
CA:108:55511 abs of J Prakt. Chem by Kunzelmann et al 328(5–6) pp. 772–776 1986.*
CA:74:89150 abs of FR1590269 May 1970.*
CA:72:42524 abs of Erdoel Kohle, Erdgas, Petrochem. by Grasemann 22 (12) pp. 751–754 1969.*
CA:129:31029 abs of JP10121126, May 1998.*
CA:110:57180 abs of EP 270124, Jun. 1988.*
CA:77:61367 abs of DE 2155671, May 1972.*
CA:115:8813 abs of EP413448, Feb. 1991.*
CA:71:24076 abs of US3438799, Apr. 1969.*
F. Broich, et al., Erdoel und Kohle –Erdgas–Petrochemie, No. 5, pp. 360–364, "Die Luftoxydation von Cyclischen Kohlenwasserstoffen in Gegenwart von Borsaeure", May 1965.
W. Foerst, Ullmanns Encyclopaedie der technischen Chemie, pp. 170–177, "Oxidation von KW Mit Luft", 1970.
H. Kalenda, Ullmanns Encyclopaedie der technischen Chemie, vol. 9, p. 674, "Cyclododecanol", 1975.

* cited by examiner

*Primary Examiner*—Jean F. Vollano
(74) *Attorney, Agent, or Firm*—Oblon, Spivak, McClelland, Maier & Neustadt, P.C.

(57) ABSTRACT

A process for oxidizing a cycloalkane, includes contacting a gas with a starting mixture, to form a product mixture, where the starting mixture contains (i) a cycloalkane, (ii) boric acid, and (iii) cobalt. The gas contains oxygen, the cycloalkane has 9 to 16 carbon atoms, and the product mixture contains a cyclic alcohol. The reactor output is increased by adding the cobalt salt, so that it is possible to lower the temperature, which decreases the rate of parallel and secondary reactions.

12 Claims, No Drawings

PROCESS FOR PREPARING CYCLIC ALCOHOLS

BACKGROUND OF THE INVENTION

1. Field of the Invention

The invention relates to a novel process for preparing cyclic alcohols by oxidation of cycloalkanes having from 9 to 16 carbon atoms using oxygencontaining gases In the presence of boric acid.

2. Discussion of the Background

Cyclic alcohols having large rings are valuable intermediates in the preparation of odorants, pharmaceuticals, agrochemicals and for preparing precursors of polymers.

The oxidation of paraffins by oxygen in the presence of boric acid has long been known and is described, for example, in DRP 552 886 (1928). This oxidation predominantly halts at the alcohol stage, which is explained by the boric acid trapping the alcohol by ester formation and thus removing it from further oxidation to the ketone, and if appropriate to the carboxylic acid.

According to H. Kalenda, Ullmanns Encyklopädie der technischen Chemie (Ullmann's Encyclopedia of Industrial Chemistry), Volume 9, 1975, p. 674, cyclododecanol is prepared by oxidation of cyclododecane with boric acid, cyclododecanone, inter alia, also being formed as a secondary oxidation product. The work of F. Broich and H. Grasemann, Erdöl-Kohle-Erdgas-Petrochemie 18, 1965, pp. 360–364, is concerned with the reaction mechanism of the air oxidation of cyclic hydrocarbons. The oxidation of cyclododecane in the presence of boric acid is described here also.

Ullmanns Encyklopädie der technischen Chemie (Ullmann's Encyclopedia of Industrial Chemistry), Supplementary Volume, 1970, pp. 170–177, in the discussion of the oxidation of saturated hydrocarbons by air, also describes the oxidation of cyclohexane to cyclohexanol and cyclohexanone. Oxidation in the presence of not only cobalt, but also boric acid is described here. However, in view of the higher energy and capital costs of the boric acid process, the cobalt process has established itself in the oxidation of cyclohexane.

In the oxidation of cyclododecane to cyclododecanol and cyclododecanone, in contrast, only boric acid is employed, because this has achieved yields of cyclododecanol/cyclodecanone-mixtures of 75 to 80%, even in the conversion range of 25 to 30%. In contrast, the oxidation of small rings is carried out using cobalt catalysts. Thus, for example, U.S. Pat. No. 4,263,453 discloses that cyclohexane can be oxidized to adipic acid using, for example, cobalt acetate.

According to EP-A-0 519 569, preferably, cycloalkanes having from 3 to 8 carbon atoms are oxidized on a molecular sieve comprising cobalt(II) ions. Cyclohexane predominantly produces cyclohexanol, cyclohexanone and adipic acid.

In the oxidation of cyclohexanol to cyclohexanol and cyclohexanone according to U.S. Pat. No. 5,767,320, a solid phthalocyanine or porphyrin complex of a transition metal is used as a catalyst. In this publication, cobalt complexes are also used in the examples. However, the process is restricted to cyclohexane and is carried out without boric acid.

SUMMARY OF THE INVENTION

An object of the present invention is to increase the reaction rate of the oxidation of large rings having from 9 to 16 carbon atoms to cyclic alcohols with boric acid, without impairing the selectivity of the reaction.

The object is achieved charging the cycloalkane and from 0.2 to 5% by weight of boric acid, based on the cycloalkane, adding during the reaction sufficient boric acid so that the molar ratio of cyclic alcohol formed to the boric acid at the end of the reaction is from 1:0.6 to 1:1.7 and, furthermore, performing the reaction in the presence of from 0.05 to 5% by weight of cobalt(II), based on the cycloalkane originally charged. Surprisingly, the feeding of boric acid and the addition of cobalt(II) lead to a significant increase in the oxidation reaction rate.

DETAILED DESCRIPTION OF THE INVENTION

In the oxidation reaction, preferably, a molar ratio of cyclic alcohol formed to boric acid of from 1:0.8 to 1:1.4 is established, roughly equimolar amounts being very particularly favorable. During the reaction, the boric acid is preferably added in from 1 to 10 portions. Boric acid may also be added continuously.

For the oxidation, use is preferably made of α-metaboric acid or a boric acid which forms α-metaboric acid, for example, such as orthoboric acid, which dehydrates to form α-metaboric acid at the oxidation temperatures.

The concentration of cobalt(II) is preferably from 0.1 to 2% by weight, based on the amount of cycloalkane at the start of the reaction. This is based on the cobalt ion and not the cobalt salt. Cobalt(II) is generally used as an organic or inorganic salt. Preferably, salts or carboxylic acids having from 2 to 18 carbon atoms are used. Examples of these are acetate, oxalate, dodecanoate, palmitate and stearate, and mixtures thereof.

The oxidizing gases preferably comprise from 10 to 100% oxygen, air being very particularly preferred as an oxidizing agent for cost and safety reasons.

Examples of large rings are cyclononane, cyclodecane, cyclododecane, cyclotridecane and cyclohexadecane. Preferably, cycloalkanes having from 10 to 14 carbon atoms are used.

The oxidation process essentially yields a reaction mixture of cycloalkanol boric ester, cycloalkanone and cycloalkane. In a further process step, the reaction product may be subjected to hydrolysis with water at elevated temperatures. The resulting product breaks down on cooling into 2 phases, an organic phase having the cycloalkanol, the cycloalkanone and the cycloalkane, and an aqueous phase having the boric acid and the cobalt. The organic phase is cobalt-free. Boric acid can be separated off from the aqueous phase by crystallization, whereupon boric acid and cobalt can be recycled to the oxidation process.

When referring to the presence of, or an amount of, a cycloalkanol or boric acid, cycloalkanol boric acid esters are included, with the weight or molar amount corresponding to weight or molar amount of the respective compound which would result after complete hydrolysis.

EXAMPLES

Having generally described this invention, a further understanding can be obtained by reference to certain specific examples which are provided herein for purposes of illustration only and are not intended to be limiting unless otherwise specified.

Comparison Example A 4.3 kg of cyclododecane (CDAN), which is enriched with alkyl peroxides (approximately 75 ppm of active oxygen)

are charged into a semicontinuously operated 6-1 stirred-tank reactor and heated to 145° C. 121 g of orthoboric acid are then added, whereupon oxidation is initiated by feeding air at 600 l (S.T.P.)/h. The oxidation period is 90 minutes.

| | |
|---|---|
| CDAN conversion rate | 2.8% |
| Yield of cyclododecanol/cyclododecanone mixture | 2.7% |
| Selectivity based on the cyclododecanol/cyclododecanone mixture | 96.4% |

Example 1

The procedure as in Comparison Example A is followed. However, 3.84 kg of CDAN are charged and, at the start of the oxidation, 85.5 g of orthoboric acid and 40.5 g of cobalt(II) acetate are added. After 60 minutes, 36.3 g of orthoboric acid are added. The reaction period is 90 minutes in total.

| | |
|---|---|
| CDAN conversion rate | 9% |
| Yield of cyclododecanol/cyclododecanone mixture | 8% |
| Selectivity based on the mixture | 89% |

Comparison Example A and Example 1 show that the addition of a cobalt salt and the feed of the boric acid lead to a multifold increase in the oxidation rate at a constant temperature of 145° C.

Comparison Example B

As in Comparison Example A, 4.3 kg of CDAN are charged into a 6-1 stirred-tank reactor and heated to 145° C. After addition of 119 g of orthoboric acid and feeding air at 600 l (S.T.P.)/h, the oxidation is initiated. 51 g of orthoboric acid are added after 60 minutes and 40 g after 185 minutes, so that in total, 210 g of orthoboric acid are added. The oxidation period is 300 minutes in total.

| | |
|---|---|
| CDAN conversion rate | 10.4% |
| Yield of cyclododecanol/cyclododecanone mixture | 9.5% |
| Selectivity based on the mixture | 90.6% |

Example 2

The procedure as in Example 1 is followed. However, the total reaction time is 180 minutes. In addition, after 90 minutes, a further 70 g of orthoboric acid are added, so that in total, 191.8 g of orthoboric acid are added.

| | |
|---|---|
| CDAN conversion rate | 22.6% |
| Yield of cyclododecanol/cyclododecanone mixture | 18.4% |
| Selectivity based on the mixture | 81.4% |

Comparison Example B and Example 2 show that the process according to the invention firstly leads to a significant increase of the reactor output and secondly, even in the region of high conversion rates, leads to very good yields of valuable products.

Comparison Example C

The procedure as in Comparison Example B is followed. However, the reaction temperature is 155° C. and the reaction time 180 minutes. In addition, 118.3 g of orthoboric acid are charged, and, during the reaction, 52.5 g of orthoboric acid are fed after 30 minutes and a further 39.2 g after 90 minutes, so that 210 g of orthoboric acid are added in total.

| | |
|---|---|
| CDAN conversion rate | 16.6% |
| Yield of cyclododecano/cyclododecanone mixture | 14.0% |
| Selectivity based on the mixture | 84.2% |

Comparison Example C and Example 2 show that the process according to the invention, despite a lower temperature, leads to a higher conversion rate, which increases the reactor output.

Example 3
Work-Up of the Oxidized Material from Example 1

The oxidized material, after the reaction, is admixed with 5 l of water at 50° C., hydrolyzing the boric esters. The resulting phases are separated. The aqueous phase comprises the boric acid and >98% of the cobalt used in the oxidation. The organic phase comprises CDAN, cyclododecanol, cyclododecanone and oxidation byproducts. The cobalt content is 16 wppm of Co. The organic phase is again washed with 2 l of water. Cobalt is no longer detectable thereafter (<1 wppm of Co).

The examples according to the invention verify that cyclic alcohols are prepared at an increased reaction rate and thus improved conversion rates. The quality of the product is unchanged, since the cobalt additionally used is quantitatively separated off.

Obviously, numerous modifications and variations of the present invention are possible in light of the above teachings. It is therefore to be understood that within the scope of the appended claims, the invention may be practiced otherwise than as specifically described herein.

The priority document of the present application, German Patent Application No. 19848730.4, filed Oct. 22, 1998, is hereby incorporated by reference.

What is claimed is:

1. A process for oxidizing a cycloalkane, comprising:
   at the beginning of the oxidation, reacting (i) a cycloalkane having 9 to 16 carbon atoms, (ii) 0.2 to 5% by weight of boric acid, based on the amount of cycloalkane, and (iii) 0.05 to 5% by weight of cobalt (II), based on the amount of cycloalkane, with an oxygen-containing gas to oxidize the cycloalkane;
   adding additional boric acid to the reactants to complete the addition of boric acid during the oxidization reaction which occurs so that in the termination phase of the oxidation reaction the molar ratio of cyclic alcohol product to boric acid in the product mixture obtained ranges from 1:0.6 to 1:1.7; and
   obtaining a product mixture containing cyclic alcohol product.

2. The process of claim 1, wherein said molar ratio of cyclic alcohol product to boric acid in the product mixture obtained ranges from 1:0.8 to 1:1.4.

3. The process of claim 1, wherein said additional boric acid is added in 1 to 10 portions.

4. The process of claim 1, wherein said additional boric acid is added continuously to the reaction medium as the reaction proceeds.

5. The process of claim 1, wherein said boric acid is α-metaboric acid, or said boric acid forms α-metaboric acid.

6. The process of claim 1, wherein said amount of cobalt (II) ranges from 0.1 to 2% by weight.

7. The process of claim 1, wherein said cobalt (II) is in the form of a cobalt (II) salt of a carboxylic acid having from 2 to 18 carbon atoms.

8. The process of claim 1, wherein said gas is air.

9. The process of claim 1, wherein said cycloalkane has 10 to 14 carbon atoms.

10. The process of claim 1, further comprising, adding water to said product mixture to form a two phase mixture comprising an aqueous phase and an organic phase.

11. The process of claim 10, further comprising, separating said aqueous phase from said organic phase.

12. The process of claim 11, further comprising: crystallizing boric acid from the separated aqueous phase and separating the crystals of boric acid obtained from the aqueous phase, and then recycling the crystals of boric acid and cobalt (II) salt to the process of oxidizing a cycloalkane.

* * * * *